United States Patent [19]

Oka et al.

[11] Patent Number: 4,562,725
[45] Date of Patent: Jan. 7, 1986

[54] MOISTURE SENSOR AND A PROCESS FOR THE PRODUCTION THEREOF

[75] Inventors: Shotaro Oka, Muko; Shu Tahara, Nagaokakyo; Junya Kobayashi, Kyoto, all of Japan

[73] Assignee: Shimadzu Corporation, Kyoto, Japan

[21] Appl. No.: 516,959

[22] Filed: Jul. 25, 1983

[30] Foreign Application Priority Data

Jul. 31, 1982 [JP] Japan .................. 57-134310
Feb. 28, 1983 [JP] Japan .................. 58-33254
Mar. 31, 1983 [JP] Japan .................. 58-57513

[51] Int. Cl.$^4$ ............................................. G01N 31/00
[52] U.S. Cl. .................................... 73/29; 73/336.5; 204/430; 338/34; 427/38; 427/41; 427/58
[58] Field of Search ............. 204/1 W, 430, 164, 165; 338/34, 35; 73/335, 29, 336.5, 23; 427/38, 41, 58

[56] References Cited

U.S. PATENT DOCUMENTS

| | | | |
|---|---|---|---|
| 2,728,831 | 12/1955 | Pope | 338/35 |
| 3,056,935 | 10/1962 | Jensen | 338/34 X |
| 3,247,478 | 4/1966 | Craig | 338/35 |
| 3,387,991 | 6/1968 | Erchak et al. | 427/41 X |
| 3,559,456 | 2/1971 | Lomker et al. | 73/336.5 X |
| 3,671,913 | 6/1972 | Mamiya et al. | 73/336.5 X |
| 3,891,958 | 6/1975 | Wakabayashi | 338/34 X |
| 3,983,527 | 9/1976 | Ohsato et al. | 338/35 |
| 4,343,688 | 8/1982 | Harwood | 204/430 |
| 4,386,336 | 5/1983 | Kinomoto et al. | 338/35 |

Primary Examiner—Andrew H. Metz
Assistant Examiner—Nam X. Nguyen
Attorney, Agent, or Firm—Stiefel, Gross, Kurland & Pavane

[57] ABSTRACT

A novel moisture sensor which comprises a moisture sensitive film formed either between a pair of electrodes or on any of the electrode which are formed on a solid substrate for a moisture sensor, said moisture sensitive film is made of a plasma polymerized polymer thin film having hydrophilic groups incorporated into its surface layer, which shows an excellent resistance to water and chemicals and a good moisture responsibility, and a process for the production thereof; and a moisture measuring cell which has the aforesaid moisture sensor and is equipped with a sample inlet part and an outlet part.

22 Claims, 18 Drawing Figures

MOISTURE SENSOR AND A PROCESS FOR THE PRODUCTION THEREOF

BACKGROUND OF THE INVENTION

1. Field of the Invention

This invention relates to moisture sensors and a process for the production thereof. This invention provides moisture sensors which have good resistance to water and resistance to chemicals, which also have good and stable performance, and which may be produced simply and conveniently.

2. Description of the Prior Art

Heretofore, as moisture sensitive substances in moisture sensors, there have been those employing ceramics, metal oxides, polyelectrolytes etc. Among those, it is known that moisture sensors employing a polyelectrolyte as a moisture sensitive substance and forming its films on various solid substrates (insulating materials, piezoelectric materials, semi-conductor materials etc.) are comparatively good in sensitivity and responsiveness.

Especially, there have been proposed various types of piezoelectric moisture sensors in which polyelectrolyte films are formed as a moisture sensitive substance on a piezoelectric element such as quartz crystal oscillator etc. and which determines the moisture utilizing as the index the change in the oscillating frequency of the quartz crystal oscillator based on the change in the weight due to the interaction (mainly hygroscopic action) between said polyelectrolyte and the moisture. The aforesaid moisture sensors are usually produced by forming first a pair of electrodes of an electrically conductive material, such as gold, silver etc., to cover a piezoelectric element plate by deposition and then forming on these electrodes a film of a polyelectrolyte which has been prepared beforehand (for example, styrene-divinylbenzene copolymer sulfonate, polystyrene sulfonate, mixtures of polystyrene sulfonate and polyvinyl alcohol, mixtures of polyvinyl alcohol and methycellulose sulfonate etc.) by such techniques as brush coating, spinner coating etc.

With the moisture sensors obtained by such a process, however, since the moisture sensitive film, i.e. the polyelectrolyte film, has been formed by coating, the adhesion with the electrode surface was not adequate, and in particular, on microanalyzing a trace water content, the moisture detecting performance was unstable and the responsiveness was also inadequate. Further, there has been a problem that the resistance to water and resistance to chemicals of the moisture sensitive film were not adequate and the use conditions was restricted thereby, and in addition, there was also a problem associated with the production that the control of the thickness of the moisture sensitive film was difficult.

On the other hand, there has also been known a moisture sensor in a form of an pair of electrodes on an insulating material and a polyelectrolyte film provided by coating between these electrodes. This moisture sensor is of a type for measuring the moisture based on the change in the electrical resistance or the electrical capacity by the water absorbed by the polyelectrolyte film, and also this type of the moisture sensor had problems with the polyelectrolyte film similar to those associated with aforesaid piezoelectric moisture sensors.

To solve the above-described problems associated with the moisture sensitive films in the moisture sensors, there have heretofore been made various proposals.

A first example is a proposal of moisture sensors of a resistance type (impedance detection) which improves the resistance to water and resistance to chemicals by forming a moisture-permeable protective polymer such as silicone resin on a polyelectrolyte film or by crosslinking a polyelectrolyte film either by ultraviolet irradiation or by employing a crosslinkable polymer [S. Miyoshi et al., "Thin-Film Humidity Sensors of Ion-Conductive Polymer", *Sharp Technical Report*, pp. 51–56, Vol. 22 (1982)]. However, such a moisture sensitive film leaves much to be desired in point of the responsiveness to the trace water content and the film thickness control.

Further, there has been proposed in Japanese Patent Application Laid-open No. 54840/1982 a piezoelectric moisture sensor which has an improved adhesion between a moisture sensitive film and a piezoelectric element plate by making said piezoelectric element plate porous.

Still further, there has also been proposed a moisture sensor of an electric capacity type which comprises a plasma polymerized polystyrene film formed as a moisture sensitive film between electrodes on an insulating substrate [S. Takeda, "Dielectric Properties of Polystyrene Thin Films Formed by rf Electrodeless Excitation", *Journal of Applied Physics*, pp. 5480–5481, No. 12, Vol. 47 (1976) and "Capacitive Humidity Element Using Polystyrene Thin Films by Plasma Polymerization", *Journal of Applied Physics*, pp. 1219–1224, No. 7, Vol. 20 (1981)]. However, the change in the capacity according to the change in the moisture was small, and also where the aforesaid film was applied to a piezoelectric moisture sensor, adequate response as moisture sensor was not obtained and thus unsatisfactory.

This invention has been made in order to eliminate the above-described various problems associated with the conventional methods. The present inventors have been intensively studying on this subject and, as a result, have discovered that by conducting plasma polymerization for the basic formation of a moisture sensitive film and further by incorporating hydrophilic groups into the plasma polymerized polymer film by chemical treatment, a moisture sensitive film which possesses excellent resistance to water, resistance to chemicals and adhesion coupled with excellent moisture responsiveness may be obtained, thereby having accomplished this invention.

SUMMARY OF THE INVENTION

Accordingly, according to this invention, there is provided a moisture sensor which comprises a moisture sensitive film formed either between a pair of electrodes or on any of the electrodes which are formed on a solid substrate for a moisture sensor, which moisture sensor is characterized by the moisture sensitive film is made of a plasma polymerized polymer thin film having hydrophilic groups incorporated into its surface layer, and a process for the production thereof.

Further, according to this invention, there is also provided a moisture measuring cell which incorporates the aforesaid moisture sensor and is equipped with a sample inlet part and an outlet part.

DETAILED DESCRIPTION OF THE PREFERRED EMBODIMENTS

The most important feature of this invention is that the moisture sensitive thin film is formed, either between a pair of electrodes or on at least one of the electrodes, by in-situ plasma polymerization of monomers, followed by incorporation of hydrophilic groups into the polymerized material, particularly into the surface layer of it. Since this is of such a construction, it is believed that the adhesion to the electrode surface and the moisture sensitive film is excellent and further the resistance to chemicals, resistance to water and response are good.

Generally, as the hydrophilic groups, hydroxyl groups and ion exchange groups may be mentioned, and the ion exchange groups known in the field of the so-called ion exchange resins may be suitably applied. Specific examples thereof include sulfonate groups, quaternary ammonium groups, phosphonate groups etc. among which the sulfonate groups are preferred. Therefore, the base, i.e. the plasma polymerized polymer thin film in which these hydrophilic groups are to be incorporated is suitably that which basically easily permits the addition of the hydrophilic groups. In general, vinyl aromatic polymers such as polystyrene, styrene-divinylbenzene copolymers, styrene-vinyl alcohol copolymers etc., vinyl alcohol-methyl-cellulose copolymers etc. are suitable, the vinyl aromatic polymers being preferred. However, even a monomer not having a functional group such as a vinyl group can be polymerized by plasma polymerization, and therefore, for example, polybenzene, polyparaffins etc. can also be applied, and thus as long as a polymer thin film is prepared by plasma polymerization, it may be employed as a substrate for a moisture detecting film. The thickness of this film is suitably about 0.01–10 $\mu$m, preferably about 0.1–1 $\mu$m.

Since such a polymer thin film of this invention has a high degree of crosslinking and has a molecular structure completely different from that produced by the conventional process which does not involve plasma polymerization and hence it is generally slightly soluble in organic solvents, it is adequately distinguishable from the conventional polyelectrolyte covering layers in this point. Further, since the hydrophilic groups have been incorporated into its surface layer, it is also adequately distinguishable from mere plasma polymerized films.

The solid substrate for a moisture sensor of this invention is selected according to the intended detecting method. That is, where the moisture is to be detected based on the change in the electrical resistance or capacity of the moisture sensitive film, an insulating material or a semi-conductor element (for example, glass, ceramics, MOSFET, MISFET) may be employed, whereas where it is based on the change in the weight, a piezoelectric element may be employed. Among these, it is preferred to employ a piezoelectric element since the effect of the moisture sensitive film in this invention is most effectively manifested. As such a piezoelectric element, a variety of substances known as showing piezoelectric characteristics in this field may be employed, and specific examples include quartz crystal oscillator, tourmaline, Rochelle salt, barium titanate, zinc oxide etc. The most preferred is quartz crystal oscillator. Further, as the electrodes of this invention, any conductive material may be employed, and specifically a thin film of a less corrosive metal, such as gold, silver etc., is suitable. Generally, when a moisture sensor of a resistance type or a capacity type is intended, a pair of thin film electrodes (especially comb-shaped electrodes) may be provided on one side of an insulating plate and between these electrodes the aforesaid moisture sensitive film may be formed so as also to cover both electrodes. On the other hand, when piezoelectric moisture sensor is intended, a thin film electrode may be formed on each side of a piezoelectric element plate and the aforesaid moisture sensitive film may be formed on at least one electrode. However, if FET (Field Effect Transistor) is employed as the solid substrate, since the electrodes are inherently increased, it is enough to form a moisture sensitive film on a gate.

Figure 1:
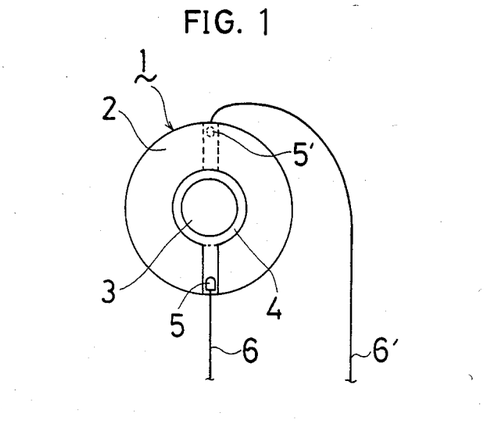
FIG. 1 is a plan view showing a specific example of a moisture sensor of this invention.
Figure 2:
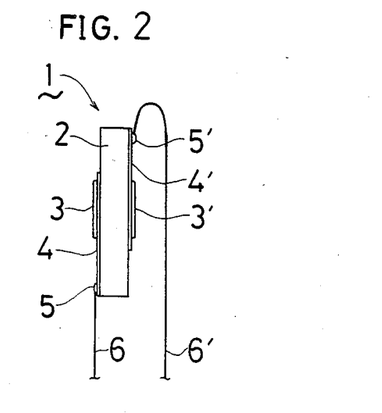
FIG. 2 is a side view of the moisture sensor of FIG. 1.

A specific example of a moisture sensor of this invention (a piezoelectric moisture sensor) is shown in FIG. 1 and FIG. 2. In the figures, the moisture sensor (1) of this invention is composed of a piezoelectric element plate (2) made of a disc-shaped quartz crystal oscillator each surface of which is provided with each of a pair of plasma polymerized polystyrene thin films (3) and (3') having sodium sulfonate groups incorporated in the surface layer via circular electrodes made of gold-deposited films (4) and (4') respectively. And, two leads (6) and (6') are connected to the ends of the electrodes (4) and (4') through terminals (5) and (5'), and the other ends of the leads (6) and (6') are connected to a frequency meter and a moisture indicator (not shown in the figures). By placing the aforesaid moisture sensor (1) so that the polystyrene thin films (3) and (3') be exposed to the object to be measured and by detecting the change in the frequency of the quartz crystal oscillator at that time by the frequency meter, the moisture may be sharply and stably measured by the moisture indicator.

Figure 3:
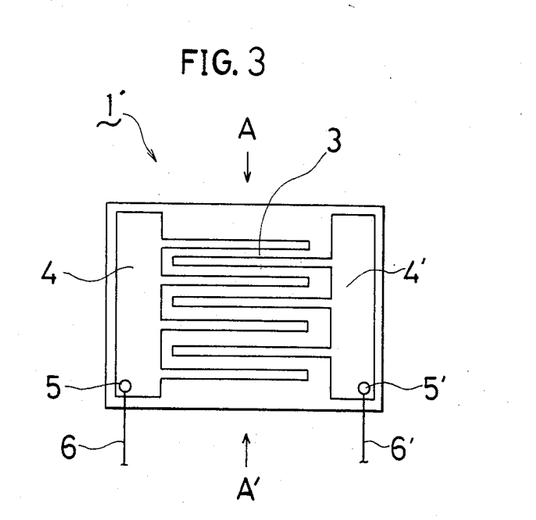
FIG. 3 is a plan view showing another specific example of a moisture sensor of this invention.
Figure 4:
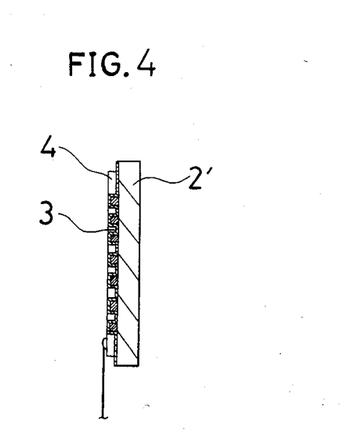
FIG. 4 is a cross-sectional view of FIG. 3 cut along Line A—A'.

On the other hand, another specific example (a moisture sensor of a resistance type) is shown in FIG. 3 and FIG. 4. In the figures, the moisture sensor (1') of this invention is composed of an insulating substrate (2') made of either side of which is provided with comb-shaped electrodes (4) and (4') made of gold-deposited films on which a plasma polymerized polystyrene thin film (3) having sodium sulfonate groups incorporated therein is formed to cover it. And, two leads (6) and (6') are connected to the ends of the electrodes (4) and (4') via terminals (5) and (5'), and said leads (6) and (6') are connected to an electric resistance meter or an impedance meter and a moisture indicator.

In the above specific examples, the film thickness of the electrodes (4) and (4') is about 1μm and the film thickness of the plasma polymerized polystyrene is about 0.4 μm.

The moisture sensor of this invention may be generally produced by forming a pair of electrodes adherently on either side or both side of a solid substrate by deposition, subjecting the resulting substrate to plasma polymerization while utilizing the electrode as a part of discharge electrode to form a desired plasma polymerized polymer film adhered to the electrode surface, and incorporating hydrophilic groups such as ion exchange groups into the surface layer of the polymer thin film by chemical treatment.

The above-described conditions for depositing the electrodes may be freely selected from the conventional known conditions. On the other hand, as the method for plasma polymerization, various methods may be applied, and generally, it is suitable to conduct glow discharge utilizing the aforesaid electrode as discharge electrode [cf. "PLASMA POLYMERIZATION OF TFE" *Journal of Polymer Science*, Vol. 19. 2937–2946(1981)], that is, to subject to the so-called low-temperature plasma polymerization conditions. Among these low temperature plasma polymerization conditions, it is preferred in point of the structure and composition of the polymer and the uniformity of the film to conduct the polymerization by low frequency discharge plasma polymerization. The frequency for that is suitably about 1 KHz. By appropriately adjusting the discharge time for the plasma polymerization, the film thickness of the polymer thin film may be controlled freely (especially between 0.01–10 μm) and accurately, thereby the scattering in the film thickness of the thin film obtained by the conventional coating method may be eliminated.

For incorporating hydrophilic groups into the surface layer of the aforesaid plasma polymerization polymer thin film, various methods such as conventional wet treatment, dry treatment etc. may be employed.

For example, where sulfonated groups are to be incorporated, it is convenient to effect that by bringing sulfuric acid gas from fuming sulfuric acid into contact with the surface of the polymer thin film at normal temperature. However, on that occasion, it is preferred to make the treating system sufficiently dry so that the formation of sulfuric acid mist may be prevented, thereby the deterioration of the polymer thin film and the corrosion of the other equipment materials may be prevented. Especially, it is more preferred to conduct gas contact treatment by making the treating system under high vacuum, and on that occasion, it is also possible to conduct discharge treatment similar to the aforesaid plasma polymerization to facilitate the incorporation of the sulfonate groups into the polymer thin film. The ion exchange groups incorporated by sulfuric acid gas are sulfonic acid groups, and in general, after the gas treatment, they may be suitably subjected to dip treatment in an aqueous salt solution, e.g. an aqueous sodium chloride solution, to convert into an ion exchanged form, i.e. sulfonate groups having metal ions.

It is difficult to determine the degree of incorporation of hydrophilic groups. However, in terms of the chemical treatment conditions, it is satisfactory to incorporate hydrophilic groups to such extent that the surface of a plasma polymerized thin film of 0.01–10 μm in thickness be brought into contact with e.g. the aforesaid sulfuric acid for about 1–120 minutes.

The moisture sensor of this invention thus obtained is good in the response to moisture and stable, further the crosslinking of the polymer thin film is high and especially it is excellent in resistance to water and resistance to chemicals, and thus it is quite useful in such respect that its uses are expanded. Furthermore, the moisture sensor of this invention does not require to make a moisture detecting substance ready beforehand as with the case of the conventional ones and also may be produced simply in a shortened time without the need of coating treatment, which leads to a cut in the cost, and is advantageous.

In particular, the sensor of this invention utilizing a piezoelectric element as shown in FIG. 1 is preferred because it is excellent in the response to a trace water content.

The sensor of this invention as described above may be presented for practical use either as such or in the form of a moisture measuring cell containing it within a container equipped with a sample inlet tube part and an outlet tube part.

Where it is used as the moisture measuring cell, there are frequently cases that water molecules are adsorbed to the innerwall surface of the container and to the innerwall surface of the sample inlet tube part and retard the response to the change in the moisture, and hence the effect of the sensor of this invention cannot be fully manifested. Particularly, in order to conduct analysis of higher accuracy by the moisture sensor, there has been put into practice a method (Rate method) for detecting the change in the response by introducing a standard gas (generally a zero gas having substantially no water content) and a sample gas alternately at constant intervals, but in such a case, the excellent responsiveness of the sensor of this invention sometimes seems to fail to manifest because of the retardation of the response.

On this point, preferred embodiments of the moisture measuring cell containing the moisture sensor of this invention therein are described hereinbelow.

One preferred embodiment of the moisture measuring cell is a moisture measuring cell equipped with a sample inlet tube part and an outlet tube part and having the aforesaid moisture sensor of this invention fixed inside, which moisture measuring cell is characterized in that a polymer film of a surface free energy of 50 erg/cm$^{-2}$ or less is formed to cover the innerwall surface of said moisture measuring cell.

By cover forming such polymer film, the adsorption of the water molecules to the innerwall surface of the container is suppressed and the retardation of the response due to the adsorption is reduced. If the surface free energy exceeds 50 erg/cm$^{-2}$, the hydrophilicity becomes too strong to substantially prevent the adsorption of the water molecules and thus this is unsuitable.

Specific examples of the polymer are polyethylene, polymethyl methacrylate, polyester type resins, polyurethane type resins etc., and those having a surface free energy of 25 erg/cm$^{-2}$ or less, generally 15-25 erg/cm$^{-2}$, for example, organopolysiloxane type polymers such as silicones and fluorinated hydrocarbon type polymers such as Teflons are preferred from a viewpoint of the adsorption preventing effect, and it is most preferred to employ organopolysiloxane type polymers considering the simplicity of cover forming etc.

As the material for the container and the construction of the sample inlet tube part and the outlet tube part used for the aforesaid moisture measuring cell, various kinds known in this field may be applied.

Usually, it is satisfactory that the aforesaid polymer film is formed to cover at least the innerwall surface of the sample inlet tube part and the innerwall surface of the moisture sensor fixed part in the moisture measuring cell, and sometimes, it may be formed to cover the entire innerwall surface of the cell also including the sample outlet tube. In any case, it is not particularly required to form it on the part to which the water content is not adsorbed.

This embodiment of the moisture measuring cell is useful particularly as an explosion-proof moisture measuring cell employing a stainless steel container. A specific example of this is shown in Example 5 described hereinbelow.

Another preferred embodiment of the moisture measuring cell is a moisture measuring cell equipped with a sample inlet tube part and an outlet tube part and having the aforesaid piezoelectric moisture sensor of this invention fixed inside, which is onstructed such that the aforesaid sample inlet tube part is composed of a standard gas inlet tube and a sample gas inlet tube and of the opening of such a sample inlet tube part is placed in the vicinity of the central part of the piezoelectric element plate, particularly in the vicinity of the central part of the moisture detecting film formed surface.

A notable feature of the aforesaid cell is that two inlet tubes, one for the sample gas and the other for the standard gas, are employed as the sample inlet tube part. Another notable point is that the openings of such two inlet tubes are constructed such that both of their opening surfaces face the central part of the piezoelectric element plate. By this, the contamination due to the water adsorption to the tube innerwall at that time when the standard gas and the sample gas are switched may be prevented, and further, the efficient gas exchange against the moisture sensitive film of the moisture sensor may be effected. Furthermore, the characteristics of the piezoelectric element plate having a high sensitivity region in the central part are also convenient.

A specific example of the opening is an opening having a dual-tube structure composed of a sample gas inlet tube and a standard gas inlet tube and the concentric opening surfaces are made close to the central part of the piezoelectric element plate on which the moisture detecting film is formed. This specific example is shown in Example 6 described hereinbelow.

A more preferred opening is an opening having a structure in which a single cavity for introducing gases wherein a sample inlet tube and a standard gas inlet tube are arranged opposite to each other and the opening surface of this cavity part is made close to the central part of the piezoelectric element plate. The measuring cell may be said an even further preferred embodiment, since, in addition to the above-described effect of the dual-tube structure, the influence by the diffusion of the retained gas in the standard gas inlet tube and the sample gas inlet tube which are separately constructed is suppressed by the respective gas pressures in the counter directions. A specific example of this is shown in Example 7 described hereinbelow.

The moisture sensors and the moisture measuring cells of this invention described above are useful for measuring the moisture or water content in various gases and, for example, they are useful for monitoring the recycled gas in the petroleum refining process and the process gas in the chlorine and fluorine chemical industry and for measuring the water content in high pressure bomb gas.

Examples of this invention are illustrated below, but it should be noted that this invention is not restricted thereto.

EXAMPLE 1

In the central part of each side of a disc-shaped quartz crystal oscillator of 0.6 mm in thickness and 14 mm in diameter were formed and adhered a pair of electrodes of gold thin films (about 1 μm in thickness) of a diameter of 8 mm by deposition. The oscillating frequency of this oscillator is about 9 Hz.

Figure 5:
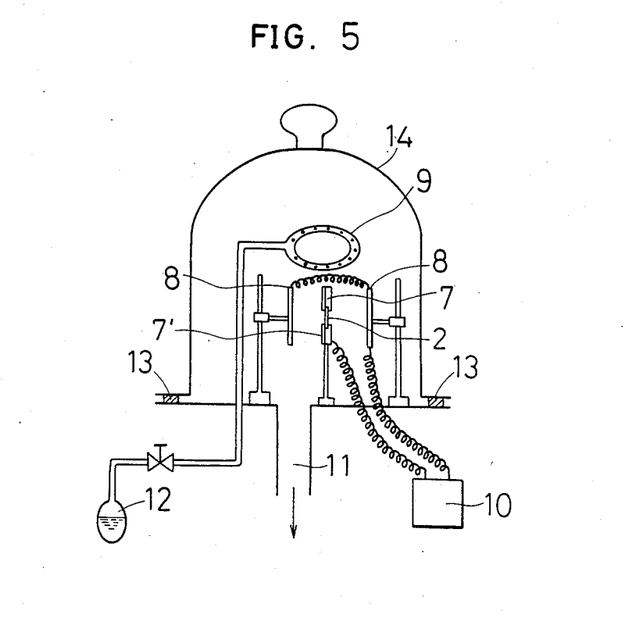
FIG. 5 is a schematic view explaining a part of the production process of a moisture sensor of this invention.

The aforesaid oscillator was set in a closed container for plasma polymerization. The construction of the plasma polymerization apparatus is shown in FIG. 5. In the figure, (7) stands for discharge electrode of aluminum, (8) similarly discharge pair of electrodes, (9) a monomer nozzle, (10) an R.F. electric source, (11) a connecting tube to a vacuum pump, (12) a styrene monomer container, (13) seals and (14) a closed container. The periphery of the aforesaid oscillator (2) is masked by a press plate (7') of aluminum so that each polystyrene thin film of 6 mm in diameter be formed in the center of each intimately adhered disc-shaped gold electrode. At that time, the press plate (7') and the gold electrodes are adequately electrically conducted. By this, the gold electrodes act as a part of the discharge electrodes. Plasma polymerization was effected using the above construction and the following conditions, thereby polystyrene thin films having a constant film thickness of about 0.4 μm were simultaneously formed on and adhered to the exposed surfaces of the gold electrodes respectively.

DISCHARGE CONDITIONS

Pressure: 1 Torr
Temperature: 25° C.
Size of Discharge Electrodes: 5×5 cm
Monomer Flow Rate: 0.25 ml/min.
Discharge Frequency: 1 kHz, 1 W
Discharge Time: 60 sec.

Figure 6:
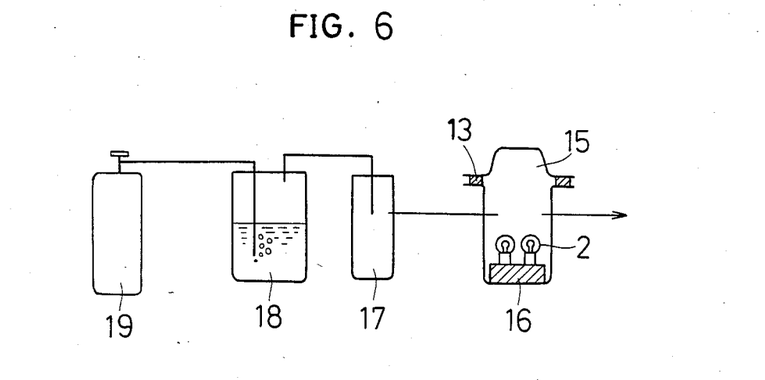
FIG. 6 is a schematic view explaining another part of the production process of a moisture sensor of this invention.

Thus, the plasma polymerized polystyrene thin films have been formed on and adhered to both surfaces of the oscillator via the gold electrodes, then the oscillator was fixed in a sulfonating tank and sulfonation was effected by introducing sulfuric acid into said tank. The construction of the sulfonating apparatus is shown in FIG. 6. In the figure, $N_2$ is passed from an $N_2$ bomb (19) at a flow rate of 0.1 l/min. The $N_2$ is bubbled through a $SO_3$ (fuming sulfuric acid) solution (18) at normal temperature and enters a buffer tank (17) with saturated $SO_3$. There, the sulfuric acid mist is removed, and only the sulfuric acid gas is introduced into the sulfonating tank (15). Inside the sulfonating tank (15) is provided a stainless steel substrate (16) and a quartz crystal oscillator is fixed by metal fixing means on this substrate. Thus, by bringing the sulfuric acid into contact with the polystyrene thin film surfaces on the quartz cyrstal oscillator, the sulfonic acid groups are incorporated into the surface layers of the polyethylene thin films. The contacting time was set about 10 minutes.

Thereafter, the aforesaid oscillator was dipped in a 1N sodium chloride solution for 30 minutes to convert the sulfonic acid groups to sodium sulfonate groups. Further, in order to remove the excess sodium chloride, it was dipped in pure water three times and dried in air to obtain a moisture sensor of this invention as shown in FIG. 1.

Figure 7:
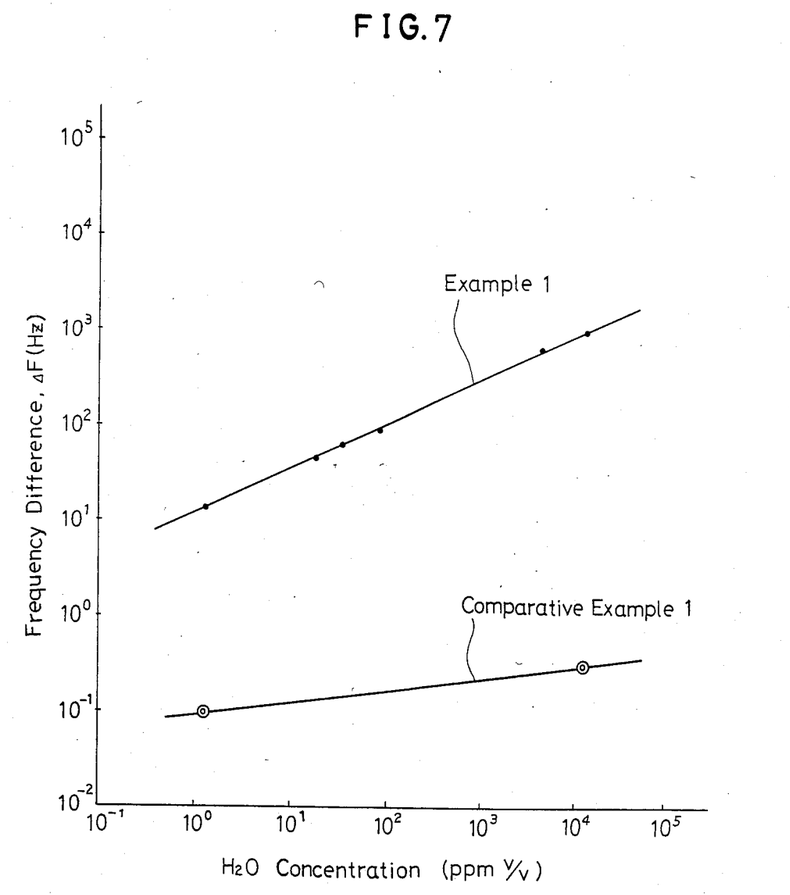
FIG. 7 is a graph illustrating the moisture response of a moisture sensor of this invention together with that of a comparative example.

The results of the test on the relation between the moisture and the Frequency Difference using this moisture sensor are shown in FIG. 7 along with those of a comparative example. This comparative example is a moisture sensor prepared similarly as in Example 1 except that the sulfonate groups have not been incorporated, that is, a moisture sensor having a moisture sensitive film composed solely of a plasma polymerized polystyrene.

Thus, it can be seen that the moisture sensor of this invention has excellent moisture responsiveness.

EXAMPLE 2 (Test on Resistance to Water)

Figure 8:
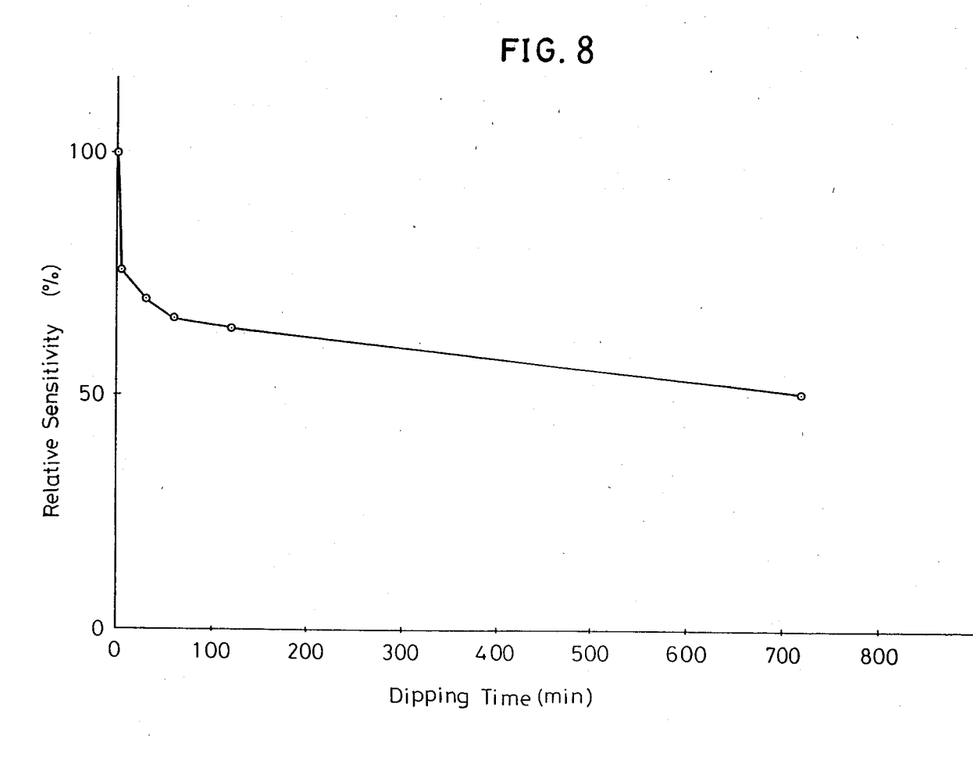
FIG. 8 is a graph illustrating the resistance to water of a moisture sensor of this invention.

The moisture sensor obtained in Example 1 was dipped in water (25° C.), and the relation between the dipping time and the sensitivity was examined. The results are set forth in FIG. 8 (in the figure, the ordinate is a scale for the sensitivity relative to the pre-dipping sensitivity taken as 100%).

Thus, although there is observed a decrease in the sensitivity over the initial period of about 5 minutes, there is only a small change in the sensitivity over the next 12 hour period, and 50% or higher sensitivity is maintained. And since the inherent sensitivity is excellent, it is found that this may well be employed for moisture measurement even immediately after such an accelerated test.

For comparison, a conventional piezoelectric moisture sensor having a polyelectrolyte film (a mixture of polyvinyl alcohol, methylcellulose and sodium polystyrene sulfonate) formed by brush coating was similarly subjected to an accelerated test, to find that the sensitivity dropped down to zero within 10 seconds.

EXAMPLE 3 (Influence of Interfering Gases and Resistance to Chemicals)

The influences on the moisture sensor obtained in Example 1 by various co-existing gas components were measured.

The results are set forth in Table 1 together with the interfering gases employed in the measurement and their concentrations. In the table, the column Comparative Example is data on the conventional moisture sensor same as the above-described one.

One the other hand, on chlorine, hydrogen sulfide, hydrogen chloride and ammonia gas, their influences on the moisture detecting film were examined respectively, to find that even after 2 month exposure, the moisture sensor of this invention still retained the initial sensitivity and thus the resistance to chemicals (resistance to corrosion) of this moisture sensitive film is excellent. This was also confirmed during the measurement on the moisture in the petroleum refining recycle gas.

TABLE 1

(Influence by Interfering Gases)

| Interfering Gas Component | Concentration of Test Gas | Interfering Influence (Corresponding to $H_2O$) ppm | |
|---|---|---|---|
| | | Moisture Sensor of Example 1 ($N_2$ Standard) | Comparative Example (Air Standard) |
| $N_2$ | 100% | 0 | 0 |
| $O_2$ | 100% | 1.1 | 0 |
| $H_2$ | 100% | 3.2 | 2.6 |
| Ar | 100% | 1.0 | — |
| CO | 100% | 0.3 | 0.7 |
| $CO_2$ | 100% | 70.3 | 44.0 |
| $Cl_2$ | 100% | 460.0 | — |
| $Cl_2$ | 765 ppm | 1.0 | — |
| HCl | 505 ppm | 0.0 | — |
| $H_2S$ | 100% | — | — |
| $NH_3$ | 100% | — | — |
| $CH_4$ | 100% | 0.1 | 1.7 |
| $C_2H_6$ | 100% | 0.1 | 1.3 |
| $C_3H_8$ | 100% | 0.0 | 0.7 |
| $C_4H_{10}$ | 100% | 0.0 | 2.6 |
| Cyclo-$C_6H_{14}$ | 10% | 3.8 | — |
| $C_2H_4$ | 100% | 0.8 | 1.3 |
| $C_3H_6$ | 100% | 0.6 | — |
| $C_6H_6$ | 9% | 9.9 | 10.0 |
| $CH_3OH$ | 12% | 3.8 | 150.0 |
| $C_2H_5OH$ | 1% | 6.9 | 1.0 |
| $C_2H_3Cl$ (monomer of vinyl chloride) | 100% | 7.0 | — |
| $CCl_2$ ($F_{12}$) | 100% | −2.2 | 7.5 |
| $CHClF_3$ ($F_{22}$) | 100% | 1.1 | 10.0 |
| $CBrF_3$ ($F_{13}B_1$) | 100% | −2.9 | — |
| $CHF_3$ ($F_{23}$) | 100% | −1.0 | — |
| $SF_6$ | 100% | −4.1 | — |

REFERENCE EXAMPLE 1

The surface analysis of the moisture sensitive film of the moisture sensor obtained in Example 1 was conducted using the ESCA. The results are set forth in FIG. 9.

Figure 9:
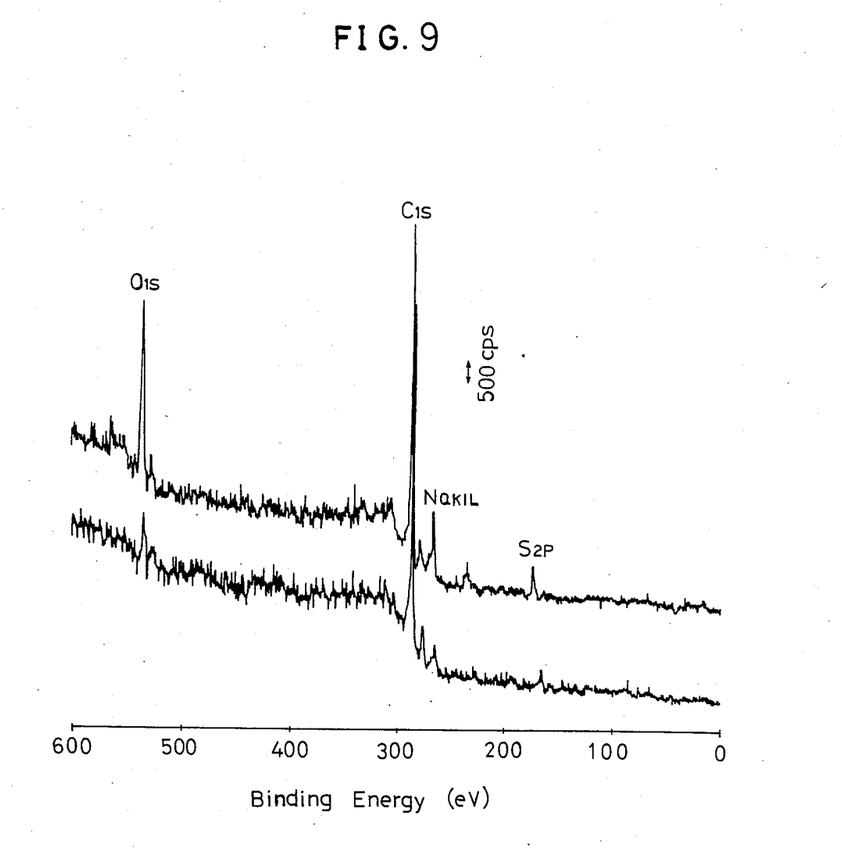
FIG. 9 is an ESCA chart illustrating the surface condition of a moisture sensitive film in a moisture sensor of this invention.

In the figure, the chart in the upper part is the results of the surface analysis before $Ar^+$ etching and the chart in the lower part is those after $Ar^+$ etching (the $Ar^+$ etching time was about 15 minutes).

As clear from the results, it has been found that the peaks of $Na_{KIL}$ and $S_{2p}$ are great before etching and small after etching, which indicates that the $-SO_3^-Na^+$ groups are present more in the surface layer of the plasma polymerized polystyrene film than inside.

EXAMPLE 4

A moisture sensor was obtained similarly as in Example 1 except that the styrene monomer in Example 1 was replaced by a mixed monomer of styrene and divinylbenzene (ratio of 2:1).

The responsiveness of this moisture sensor was more or less the same as that of the moisture sensor of Example 1.

EXAMPLE 5 (Moisture Measuring Cell)

Figure 10:
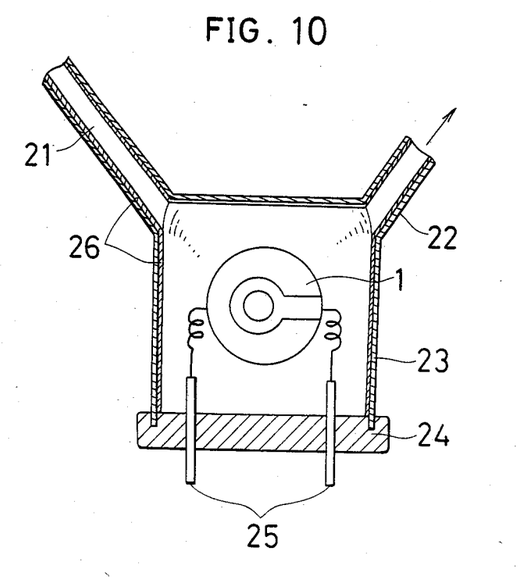
FIG. 10 is a construction illustrative figure showing an embodiment of a moisture measuring cell employing a moisture sensor of this invention.

Within a stainless steel container (23) of a parallelopipedon form (18 mm in width, 5 mm in length and 18 mm in depth and the lower part is open) equipped with a sample inlet tube part (21) and a sample outlet tube part (22), each of 1.5 mm in inner diameter and 50 mm in length, was sprayed a silicone resin liquor (a dispersion of silicon sol in 20% by weight of toluene, Trade name: Pergan-spray produced by Dow Corning Corp.) and dried to form a silicon polymer film (26) of about 0.1-2 mm to cover the innerwall surface, then a cell support (24) having a moisture sensor (1) fixed thereon was fitted to obtain a moisture measuring cell of this invention as shown in FIG. 10. Reference numeral (25) designates output pins.

As the aforesaid moisture sensor (1) was employed that obtained similarly as in Example 1 by forming a polystyrene on a quartz crystal oscillator by plasma polymerization (polymerization conditions: pressure 1 mm Hg, temperature 25° C., discharge current 70 mA, discharge voltage 500 V and discharge time 90 minutes), then sulfonating said polystyrene with $SO_3$ (sulfuric acid gas) for 30 minutes in the conventional manner, washing it with water, converting it to a sodium sulfonate using an NaCl solution, further washing with water and drying.

A gas of a constant moisture (a gas containing 20 ppm of moisture) was passed to the thus obtained moisture measuring cell through the sample inlet tube at a flow rate of 200 ml/min. at 60° C. for 2 minutes, and thereafter a zero gas (a gas containing no moisture) was passed under the same conditions for 3 minutes, and the response (A) was examined, and also, the gases were passed in reverse order and the response (B) at that time was examined. The results are set forth in FIG. 11 together with a comparative example (a similar moisture measuring cell except that the polymer film has not been formed to cover).

Figure 11:
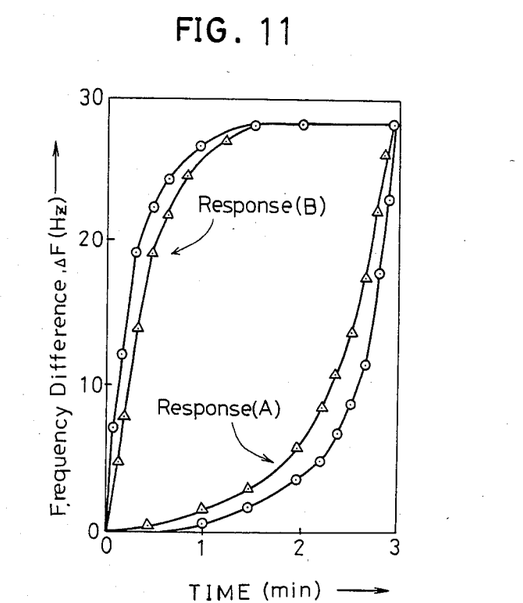
FIG. 11 is a graph illustrating the response of the moisture measuring cell shown in FIG. 10 together with that of a comparative example.

In the figure, the plot o is for the moisture cell of this invention, and the plot Δ is for the moisture measuring cell of the comparative example.

Thus, it can be seen that the aforesaid moisture measuring cell shows a higher response speed as compared with that not having a polymer film on the cell innerwall surface.

EXAMPLE 6 (Moisture Measuring Cell)

Figure 12:
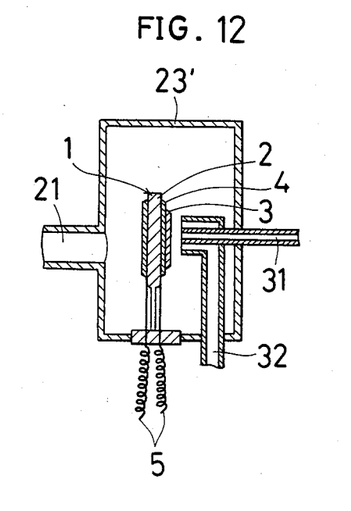
FIG. 12 is a construction illustrative figure showing another embodiment of a moisture measuring cell employing a moisture sensor of this invention.
Figure 13:
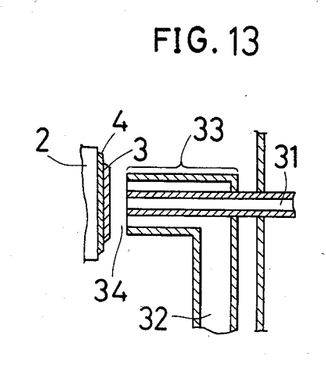
FIG. 13 is a partially enlarged figure of the main part of FIG. 12.

FIG. 12 is a construction illustrative figure showing a moisture measuring cell of this invention. In the figure, the moisture measuring cell contains a moisture sensor (1) having a moisture sensitive film (3; 5 mm in diameter) made of the aforesaid plasma polymerized polymer thin film in the central part of one side of a disc-shaped piezoelectric element plate (2) of 13.9 mm in diameter via a thin film electrode of e.g. gold (4; 5 mm in diameter), and comprises a stainless steel container for a moisture measuring cell (23'; cylindrical; inner volume of about 0.7 cm$^3$) equipped with a sample outlet tube part (21) and a sample inlet tube part consisting of a sample gas inlet tube (32) and a standard gas inlet tube (31). And, an opening (33) of the tubes (31) and (32) inside the cell are, as shown in FIG. 13, composed of a dual-tube structure, and their opening surface (14) is located so as to face opposite to and close to the vicinity of the central part of the piezoelectric element plate (2). The bore of the inner tube of the dual-tube was set 1.5 mm and the bore of its outer tube 3 mm, and the clearance from the moisture sensor 0.3 mm. Generally, in the dual-tube, the bore of the outer tube is suitably about twice that of the inner tube.

The moisture sensor used was one made in the same way as in Example 5.

Figure 14:
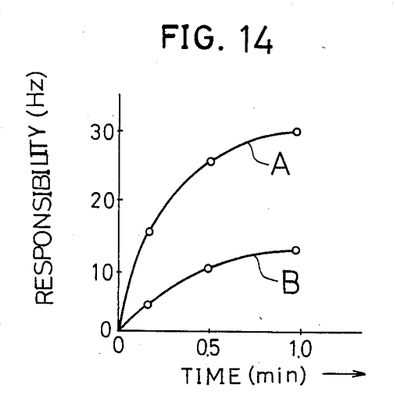
FIG. 14 is a graph showing the response of the moisture sensor of FIG. 13 together with that of a comparative example.

A moisture constant gas for a test (a normal pressure gas containing about 15 ppm of moisture in nitrogen gas) was passed to the aforesaid moisture measuring cell via the sample gas inlet tube (32) at a gas flow rate of 500 ml/min. at 25° C. and the response was examined by comparing with a control where a zero gas (nitrogen gas) was passed to the standard gas inlet tube (31). The results are shown in FIG. 14 together with a comparative example (a similar moisture measuring cell in which the sample inlet tube part was not separated). In the figure, (A) stands for the aforesaid moisture measuring cell and (B) the moisture measuring cell of the comparative example. As shown, the response of the aforesaid moisture measuring cell is excellent.

EXAMPLE 7 (Moisture Measuring Cell)

Figure 15:
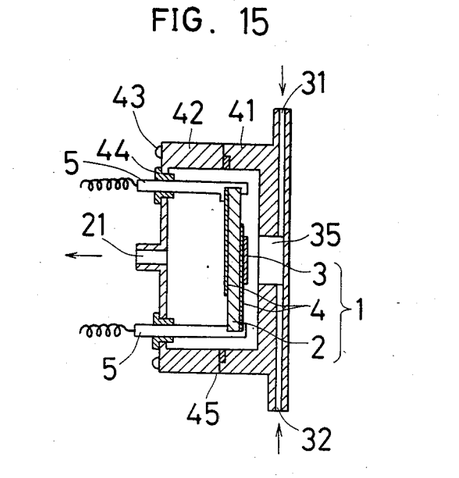
FIG. 15 is a construction illustrative figure showing a moisture sensor of this invention.

FIG. 15 is a construction illustrative figure showing a moisture measuring cell of this invention. In the figure, the moisture measuring cell is equipped with a sample inlet tube part consisting of a standard gas inlet tube (31), a sample inlet tube (32) and a cylindrical cavity-shaped gas inlet (35) and a gas outlet tube part (21) and is basically composed of a moisture sensor consisting of a piezoelectric element plate (2), a thin film electrode (4) and a moisture sensitive film (3). And, the gas inlet (35) is arranged such that its opening surface faces to the vicinity of the central part (that is, corresponding to the moisture sensitive film (3)) and is constructed such that the inlet tubes (31) and (32) are connected inside this inlet, thereby the gases from each tube (31) and (32) may be passed through the same inlet and efficiently supplied into the moisture measuring cell, in particular, to the moisture sensor. Further, the respective gas supply openings (31a) and (32a) for the aforesaid inlet tubes (31) and (32) located inside the inlet are arranged so as to face to each other. Further, reference numerals, (41) and (42) designate a cylindrical housing (inner volume of about 1.3 cm$^3$) containing the moisture sensor, (43) a screw, (44) a fixing means, (45) a packing and (5) outlet pins.

Figure 16:
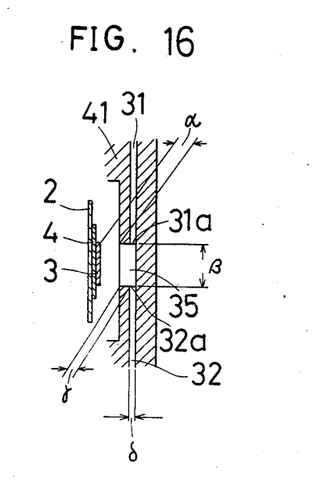
FIG. 16 is a partially enlarged figure of the main part of FIG. 15.

Further, the more detailed construction of the gas inlet tube part in the above-described example is as shown in FIG. 16, wherein the tube diameter δ of the inlet tubes (31) and (32) is set 1 mm, the bore β of the inlet (35) 5 mm (corresponding to the moisture sensitive film (3) formed in the central part of the piezoelectric element plate (2)), the depth γ of the inlet (35) 2 mm, and the distance α of the opening surface of the inlet (35) and the moisture sensitive film (3) 1 mm. The moisture sensor (1) used was the same as in Example 6.

Figure 17:
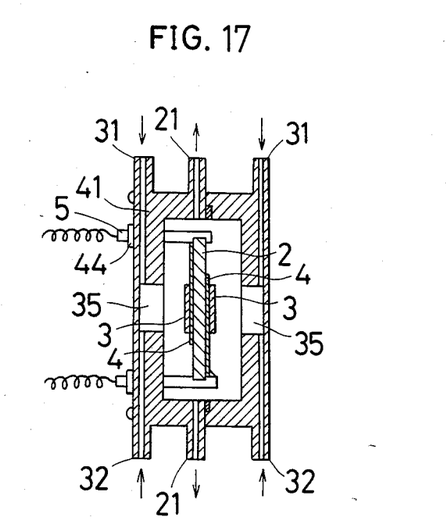
FIG. 17 is a specific example of a modification of FIG. 15.

In order to examine the influence by the gas retention as compared with the moisture sensor of Example 6, the transitional response characteristics of the moisture sensor to the water content were examined by alternately introducing 4 ppm gas ($H_2O$ in $N_2$) and a dry gas (dry $N_2$ gas) through the sample gas inlet tube and the standard gas inlet tube at one-minute intervals respectively, and as a result, there was no influence by the gas retention observed, and it was found that this was more suitable as a moisture measuring cell than the sensor in Example 6.

Where there is employed a moisture sensor in which plasma polymerized thin films having hydrophilic groups incorporated have been formed on both sides of the piezoelectric element plate, as shown in FIG. 17, it is preferred to construct two sets of gas inlet tube parts and gas outlet tube parts respectively and make them correspond to the respective sensitive films, and at that time, a detecting sensitivity about twice that of the one used in FIG. 15 is obtained.

EXAMPLE 8

Figure 18:
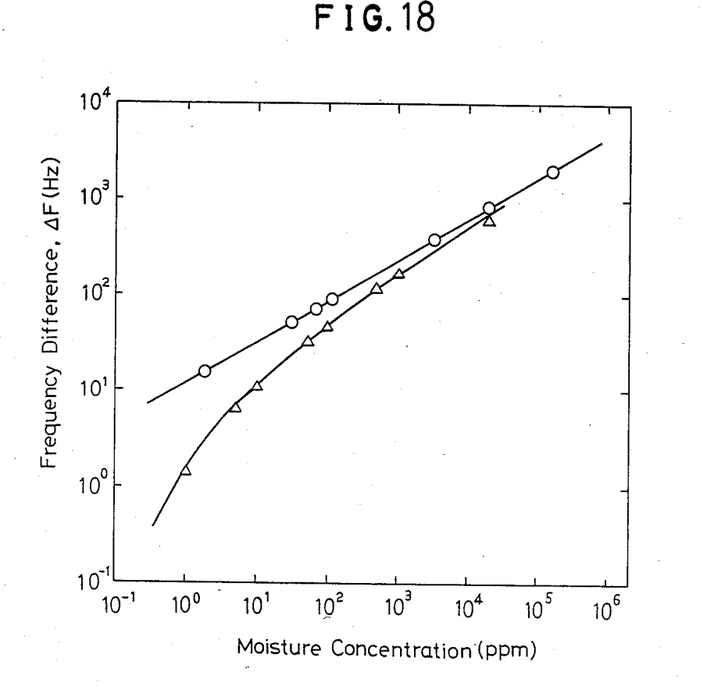
FIG. 18 is a graph illustrating the response of the moisture sensor of FIG. 15 together with that of a comparative example.

A comparison was made employing a conventional moisture measuring cell (effective volume for introducing a sample gas: 2.18 ml; the shapes of the sample inlet tube part and the outlet tube part being the same as in FIG. 10; manufactured by E. I. du Pont) containing a moisture sensor having a polymer electrolyte consisting of a mixture of polyvinyl alcohol, methylcellulose and sodium polystyrenesulfonate formed as moisture sensitive films on electrodes on a quartz crystal oscillator, and a moisture measuring cell of Example 7 (effective volume for introducing a sample gas: 0.04 ml). The comparison was conducted by measuring the change in the response to the sample gases of various degrees of moisture (Frequency Difference $\Delta F$) by Rate method. The Rate method was effected by introducing a dry gas (a zero gas) and a sample gas into the cell alternately at one-minute intervals at about 45° C. The results are shown in FIG. 18, wherein the $\Delta$ is for the conventional cell and the o is for the cell of this invention.

Thus, it can be seen that the moisture measuring cell of this invention exhibits a good linear response over the entire range from low temperatures to high temperatures.

What we claim is:

1. A moisture sensor comprising a piezoelectric material as solid substrate; a pair of electrodes in contact with said substrate; and a highly crosslinked plasma polymerized polymer thin film having an outer surface layer incorporating hydrophilic groups, said hydrophilic groups having been incorporated by chemical treatment, said film being in contact with at least one of said electrodes.

2. The moisture sensor of claim 1 in which the hydrophilic group is a hydroxy group or an ion exchange group.

3. The moisture sensor of claim 2 in which the ion exchange group is a sulfonate, quaternary ammonium or phosphonate group.

4. The moisture sensor of claim 1 in which the plasma polymerized polymer film is a vinyl aromatic polymer.

5. The moisture sensor of claim 4, in which the vinyl aromatic polymer is polystyrene, styrene-divinyl benzene copolymer or styrene-vinyl alcohol copolymer.

6. The moisture sensor of claim 1 in which the plasma polymerized polymer thin film has a thickness of about 0.01–10 $\mu$m.

7. The moisture sensor of claim 1 in which the piezoelectric material is a quartz crystal oscillator, tourmaline, Rochelle salt, barium titanate or zinc oxide.

8. The moisture sensor of claim 1 in which the solid substrate is an insulating material.

9. The moisture sensor of claim 8 in which the insulating material is glass or ceramics.

10. A process for preparing a moisture sensor comprising depositing a pair of electrodes on a piezoelectric material as a solid substrate, subjecting the resulting substrate to plasma polymerization in the presence of a desired monomer vapor to form a plasma polymerized polymer film adhering to the substrate between the electrodes or on at least one of the electrodes and incorporating hydrophilic groups into the surface layer of the polymer thin film by a chemical treatment.

11. The process of claim 10 in which the hydrophilic groups are hyroxy groups or ion exchange groups.

12. The process of claim 11 in which the ion exchange group is a sulfonate, quaternary ammonium or phosphonate group.

13. The process of claim 10 in which the plasma polymerized polymer film is a vinyl aromatic polymer.

14. The process of claim 13, in which the vinyl aromatic polymer is polystyrene, styrene-divinyl benzene copolymer or styrene-vinyl alcohol copolymer.

15. The process of claim 10 in which the plasma polymerization is conducted by a low frequency discharge plasma polymerization method.

16. A moisture measuring cell comprising a sample inlet tube part and an outlet tube part having a moisture sensor inside the cell and an innerwall surface covered by an organic polymer film having a surface free energy of up to 50 erg/cm$^{-2}$ the moisture sensor comprising a solid substrate; a pair of electrodes in contact with said substrate; and a highly crosslinked plasma polymerized polymer thin film having an outer surface layer incorporating by chemical treatment hydrophilic groups, said film being in contact with at least one of said electrodes.

17. The moisture measuring cell of claim 16 in which the organic polymer film is an organopolysiloxane or a fluorinated hydrocarbon type polymer.

18. A moisture measuring cell comprising a sample inlet tube part with an opening, an outlet tube part and a moisture sensor inside the cell, said moisture sensor comprising a piezoelectric element plate as a solid substrate, the sample inlet tube part being composed of a standard gas inlet tube and a sample gas inlet tube, the opening of the sample inlet tube part being located in the vicinity of the central part of the piezoelectric element plate and the moisture sensitive film; a pair of electrodes in contact with said substrate; and a highly crosslinked plasma polymerization polymer thin film having an outer surface layer incorporating hyrophilic groups, said hydrophilic groups having been incorporated by chemical treatment said film being in contact with at least one of said electrodes.

19. The moisture measuring cell of claim 18 in which the opening of the sample inlet tube part has a dual-tube structure.

20. The moisture measuring cell of claim 18 in which the opening of the sample inlet tube part has a single cavity for introducing gases wherein a sample inlet tube and a standard gas inlet tube are arranged opposite to each other.

21. A moisture sensor comprising a piezoelectric material as a solid substrate; a pair of electrodes in contact with said substrate; and a highly crosslinked plasma polymerized polymer thin film having an outer surface layer incorporating by chemical treatment sulfonate or quaternary ammonium groups; said film being in contact with at least one of said electrodes.

22. A process for preparing a moisture sensor comprising depositing a pair of electrodes on a piezoelectric material as a solid substrate, subjecting the resulting substrate to plasma polymerization in the presence of a monomer vapor to form a plasma polymerized polymer film adhering to the substrate between the electrodes or at least one of the electrodes and incorporating by chemical treatment sulfonate or quaternary ammonium groups into the outer layer of the polymer thin film.

* * * * *